United States Patent [19]
Suzuki

[11] Patent Number: 5,589,133
[45] Date of Patent: Dec. 31, 1996

[54] OXYGEN ELECTRODE, BIOSENSOR AND PROCESSES FOR MANUFACTURING SAME

[75] Inventor: Hiroaki Suzuki, Kawasaki, Japan

[73] Assignee: Fujitsu Limited, Kawasaki, Japan

[21] Appl. No.: 318,209

[22] Filed: Oct. 5, 1994

Related U.S. Application Data

[63] Continuation of Ser. No. 41,054, Mar. 31, 1993, abandoned.

[30] Foreign Application Priority Data

Jul. 20, 1992 [JP] Japan ................................. 4-191768

[51] Int. Cl.$^6$ ................................................ G01N 27/404
[52] U.S. Cl. ................. 422/79; 422/82.02; 435/287.5; 435/287.7; 435/817
[58] Field of Search ................................. 422/79, 82.01, 422/82.02, 82.03, 82.04, 90; 436/138, 151; 204/403, 413, 414, 415, 426, 433; 435/7.91, 7.92, 29, 817, 287.5, 287.7

[56] References Cited

U.S. PATENT DOCUMENTS

| | | | |
|---|---|---|---|
| 4,384,936 | 5/1983 | Obana et al. | 204/403 |
| 4,536,274 | 8/1985 | Papadakis et al. | 204/433 |
| 4,654,127 | 3/1987 | Baker et al. | 422/82.04 X |
| 4,717,673 | 1/1988 | Wrighton et al. | 436/138 X |
| 4,975,175 | 10/1990 | Karube et al. | 204/414 X |
| 4,999,582 | 3/1991 | Parks et al. | 422/82.02 X |
| 5,001,048 | 3/1991 | Taylor et al. | 436/151 X |
| 5,156,810 | 10/1992 | Ribi | 422/82.01 |

Primary Examiner—Jeffrey Snay
Attorney, Agent, or Firm—Staas & Halsey

[57] ABSTRACT

An oxygen electrode comprising a plastic sheet, two or three electrode patterns formed on the plastic sheet, a paraffin layer formed on the peripheral portion of the plastic sheet for delineating a sensitive area, a carrier sheet impregnated with an electrolyte and placed on the central portion or the sensitive area of the plastic sheet, and a gas permeable membrane covering the carrier sheet and the paraffin layer. A biosensor may be also provided by further providing a microorganism or enzyme-immobilized layer on the gas permeable membrane of the above oxygen electrode.

17 Claims, 7 Drawing Sheets

OXYGEN ELECTRODE, BIOSENSOR AND PROCESSES FOR MANUFACTURING SAME

This application is a continuation, of application Ser. No. 08/041,054, filed Mar. 31, 1993, now abandoned.

BACKGROUND OF THE INVENTION

1. Field of the Invention

The present invention relates to an oxygen electrode, a biosensor, and processes for manufacturing the same. The oxygen electrode is used to determine the concentration of gaseous oxygen dissolved in a liquid and the oxygen electrode may be used to make a biosensor.

2. Description of the Related Art

An oxygen electrode is composed of a working electrode (cathode) and a counter electrode (anode) in an electrolyte such as potassium chloride. The dissolved oxygen and water react with electrons on the working electrode (cathode) to generate hydroxide ions which result in electric current between the counter electrode or anode and the working electrode or cathode in an amount in linear relation to the concentration of the dissolved oxygen. With the oxygen electrode, the electric current can be measured to estimate the concentration of the dissolved oxygen. The oxygen electrode may optionally further comprise a reference electrode.

A biosensor for determining, for example, a carbon dioxide gas concentration, a concentration of a glucose or alcohol, or the like, may be realized by combining the oxygen electrode with autotrophic microorganisms, for example, one taking carbon dioxide gas as the nutrient, or various enzymes and by measuring the oxygen concentration with the oxygen electrode since the consumption of the carbon dioxide gas results in the variation of the oxygen concentration.

The oxygen electrode can be used in various industrial fields including the measurement of the biochemical oxygen demand (BOD) in water, the measurement of the dissolved oxygen as a parameter of the progress of a fermentation of glucose or alcohol in a fermentation tank, and others.

An example of the above biosensor is a glucose concentration sensor using glucose oxidase which oxydizes glucose and transforms it into gluconolactone. The glucose concentration sensor estimates the glucose concentration by using as a parameter the decrease of the dissolved oxygen concentration resulted from the above oxidation reaction. Such glucose concentration sensors are utilized in fermentation industries and the determination of blood sugar value, etc.

A typical oxygen electrode is illustrated with reference to FIG. 1, in which 1 denotes a working electrode (cathode), 2 a counter electrode (anode), 3 an electrolyte, and 4 a gas permeable membrane. The oxygen dissolved in the electrolyte through the gas permeable membrane 4 and water react with electrons on the working electrode (cathode) to form hydroxide ions OH— (i.e., $O_2+2H_2O+4e^-=4OH^-$) and cause an electric current in relation to the amount of the dissolved oxygen so that the oxygen concentration can be estimated from the electric current detected.

This oxygen electrode is however large in size and is difficult to be manufactured in mass production. The inventors have developed and disclosed a small oxygen electrode in which recesses are formed on a surface of a silicon substrate by anisotropic etching and the recesses are separated with each other, filled with an electrolyte, and covered with an oxygen permeable membrane (Japanese Unexamined Patent publication No. 63-238548; Japanese Patent Application No. 62-71739). The inventors have also developed and disclosed an improved small oxygen electrode in which anodic bonding is utilized to ease commercial manufacturing of the oxygen electrode (Japanese Unexamined Patent publication No. 04-125462; Japanese Patent Application No. 02-243849).

Nevertheless the oxygen electrodes and biosensors in the prior art are still expensive and cannot be used as disposable products. On the other hand, strong demand for such oxygen electrodes and biosensors exists and lowering of the price thereof is required.

SUMMARY OF THE INVENTION

To attain the above and other objects, the present invention provides an oxygen electrode comprising a plastic sheet, two or three electrode patterns formed on the plastic sheet, a paraffin layer formed on a peripheral portion of the plastic sheet for delineating a sensitive area, a carrier sheet impregnated with an electrolyte and placed on a central portion or the sensitive area of the plastic sheet, and a gas permeable membrane covering the carrier sheet and the paraffin layer.

The present invention further provides a biosensor comprising a plastic sheet, two or three electrode patterns formed on the plastic sheet, a paraffin layer formed on a peripheral portion of the plastic sheet for selineating area, a carrier sheet impregnated with an electrolyte and placed on a central portion or the sensitive area of the plastic sheet, a gas permeable membrane covering the carrier sheet and the paraffin layer, and an enzyme or microorganism-immobilized layer formed on the gas permeable membrane.

The plastic sheet may be any sheet which endures the heat for bonding the paraffin to the plastic sheet and includes polyester, polycarbonate, polyimide and polyetylene. The plastic sheet is typically in the form of a rectangle, but is not limited thereto.

The paraffin layer may be of any paraffin which can form a bank around the plastic sheet and includes paraffins having a softening point of about 100° to 150° C. The paraffin layer can be easily formed by cutting a paraffin sheet into a desired pattern, placing on the plastic sheet and fusing the paraffin to the plastic sheet.

The carrier sheet may be any material which can carry or absorb an electrolyte and includes a natural or synthetic paper, a nonwoven cloth, a woven cloth, etc., with a paper being preferred.

The gas permeable membrane may be any known film which is permeable to a gas, particularly oxygen and includes films of fluorinated ethylene propylene, siliconw rubber, polystylene, polypropylene, polytetrafluoroetylene or the like, with fluorinated ethylene propylene being preferred.

The electrolyte may be any known electrolyte.

Preferably, the carrier sheet further contains a gel impregnated therein. The gel has a function of preventing or decreasing a gap or an air layer in the carrier sheet after the electrolyte is impregnated therein so that trapping of gas bubbles is prevented and the life time of the oxygen electrode is increased. The gel may be any gel which fills pores in the carrier sheet and allows the electrolyte to migrate therein and includes agarose, gelatin, acrylic amide (irradiated), calcium alginate.

In accordance with the present invention, there is further provided a process for manufacturing an oxygen electrode, comprising the steps of preparing a plastic sheet, forming two or three electrode patterns on the plastic sheet, fusing a paraffin sheet onto a peripheral portion of the plastic sheet, placing a carrier sheet, preferably impregnated with a gel, on the plastic sheet in a region surrounded by the paraffin sheet, disposing a gas permeable membrane over the carrier and the paraffin sheet, and impregnating the carrier sheet with an electrolyte. Preferably, the electrode patterns are formed by selective vacuum evaporation deposition of a metal with a metal mask.

There is also provided a process for manufacturing a biosensor, comprising the steps of preparing a plastic sheet, forming two or three electrode patterns on the plastic sheet, fusing a paraffin sheet onto a peripheral portion of the plastic sheet, placing a carrier sheet, preferably impregnated with a gel, on the plastic sheet in a region surrounded by the paraffin sheet, disposing a gas permeable membrane over the carrier and the paraffin sheet, forming an enzyme or microorganism-immobilized layer on the gas permeable membrane, and impregnating the carrier sheet with an electrolyte.

These types of an oxygen electrode and biosensor can be made with a plastic sheet, a paraffin sheet, a paper, a fluorinated ethylene propylene sheet, and the like, all of which are cheap and easy to handle and machine, and, therefore, these oxygen electrode and biosensor can be manufactured at a very low price and can be used as disposable products.

DESCRIPTION OF THE PREFERRED EMBODIMENTS

The present invention will be further described with reference to the drawings. It should be noted that, although manufacture of a single oxygen electrode or biosensor will be described below, a number of oxygen electrodes or biosensors may be simultaneously manufactured in practice.

A. Oxygen Electrode (1)

Materials

A polyester sheet, an electrode substrate, was a used 100 μm-thick overhead projection transparency (Fuji Xerox, No. V 515). A 200 μm-thick paraffin film (American National Can, PARAFILM "M"), used for sealing flasks and beakers, was used to delineate the sensitive area. The electrolyte layer was recycled 100 μm-thick copier paper saturated with electrolyte. A 12 μm-thick fluorinated ethylene propylene (FEP) membrane (Toray) served as the gas-permeable membrane.

Structure

Figure 3:
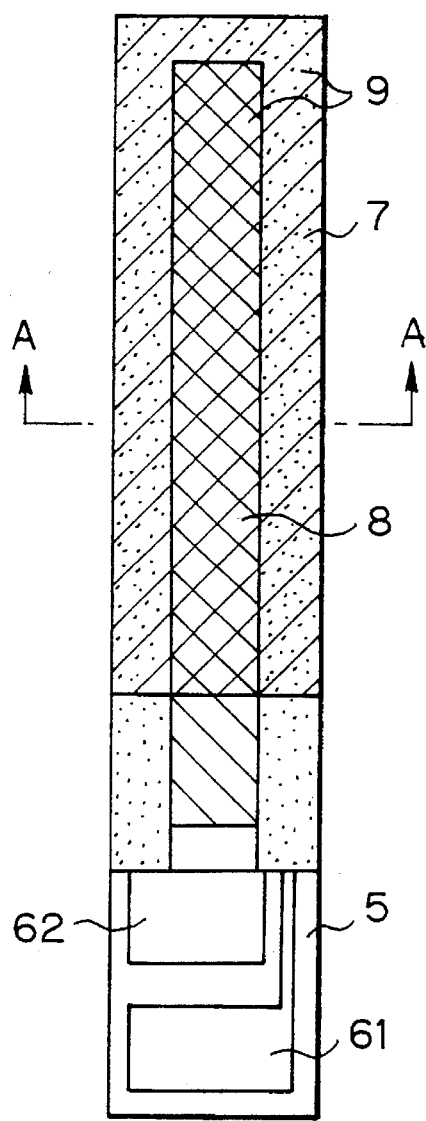
FIGS. 3 and 4 are plan and cross-sectional views of an oxygen electrode in an Example of the present invention.

Chip dimensions are 5×25 mm (FIG. 3). The electrode used were a silver cathode and a Ag/AgCl anode—a combination often used in miniature oxygen electrodes. Silver was used for the electrode leads and pads. The sensitive area was delineated with paraffin film. A rectangular piece of paper was saturated with an electrolyte solution of 0.1M KCl dissolved in 50 mM Tris/HCl buffer (pH 8.5). The area where the paper spans the cathode and anode forms the active area. The cathode was 0.2×2 mm and the anode was 9.5×2 mm. The polyester sheet was covered with an FEP gas-permeable membrane.

Our experience with previous oxygen electrodes suggests that even small amounts of hydrogen peroxide accumulating over time after oxygen reduction adversely affected electrode response. Oxygen completely reduced to OH− by four-electron transfer would leave the output current unaffected and stable. However, even a little hydrogen peroxide is left unreacted, it will be gradually accumulated in the sensitive area, some oxidized on the anode producing oxygen, and affecting the electrode response, especially when the electrode operates for a long time. The paper was used to suppress the crosstalk. To reduce the cross talk more effectively, the cathode and anode were 4.8 mm apart. Beside oxygen production on the anode, air layer can spread from the anode side through the gap between the paper and the polyester sheet. To prevent an air layer from spreading from the anode through the gap between the paper and polyester sheet, the paper and polyester sheet may be laminated with a thin paraffin layer.

The electrode is not charged with an electrolyte until ready for use, making it usable as long as it is kept out of direct contact with atmosphere that would tarnish the silver.

Fabrication

Figure 1:
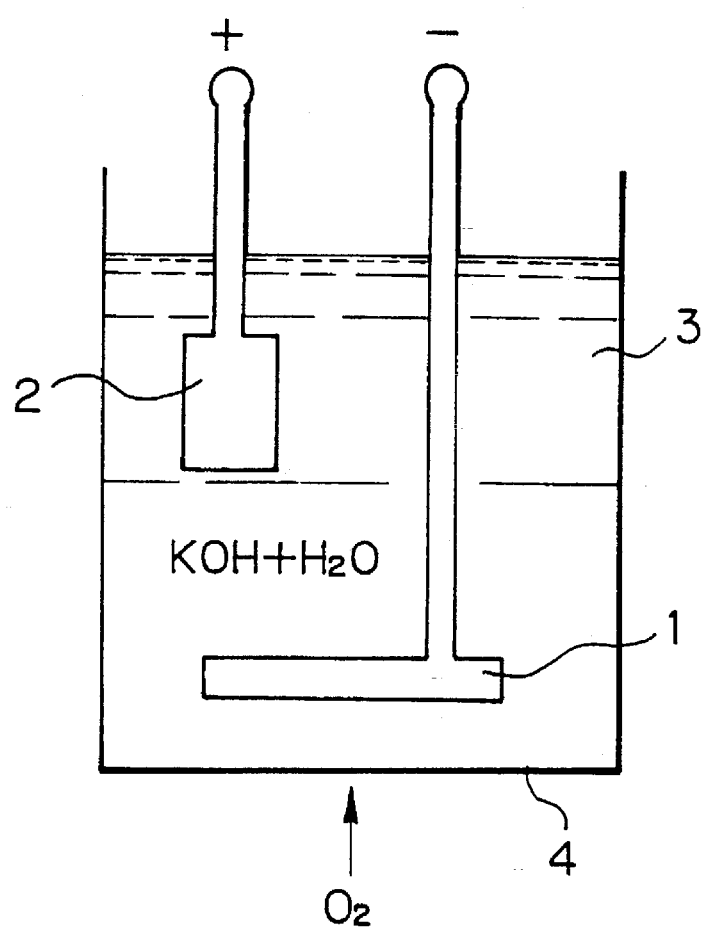
FIG. 1 schematically shows an oxygen electrode in the prior art.
Figure 2C:
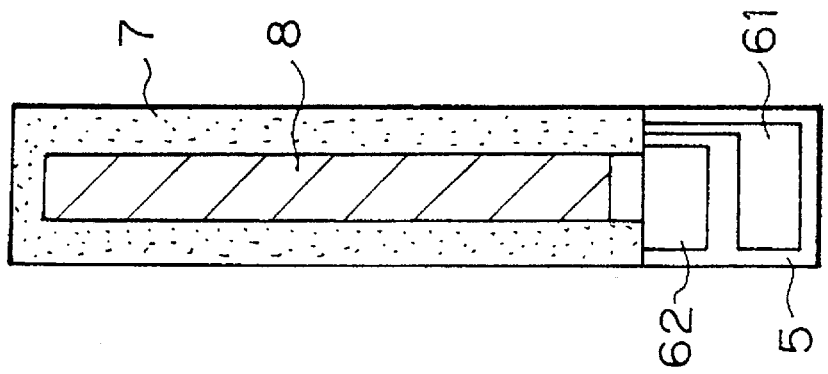
FIGS. 2A to 2C are plan views of an oxygen electrode in an Example of the present invention in the main manufacturing steps.
Figure 2B:
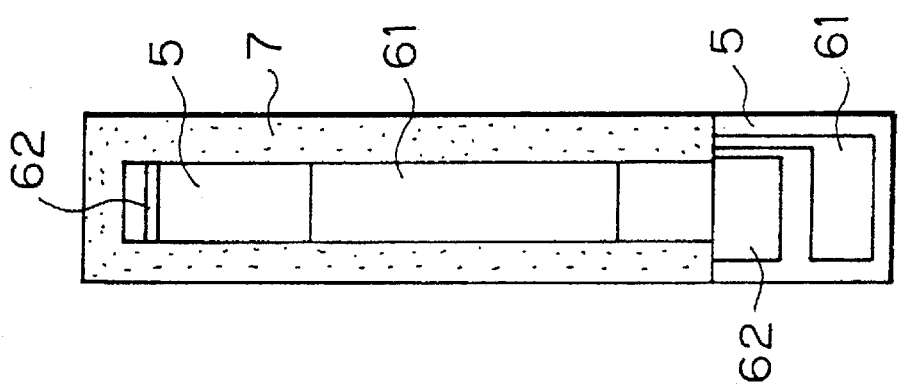
Figure 2A:
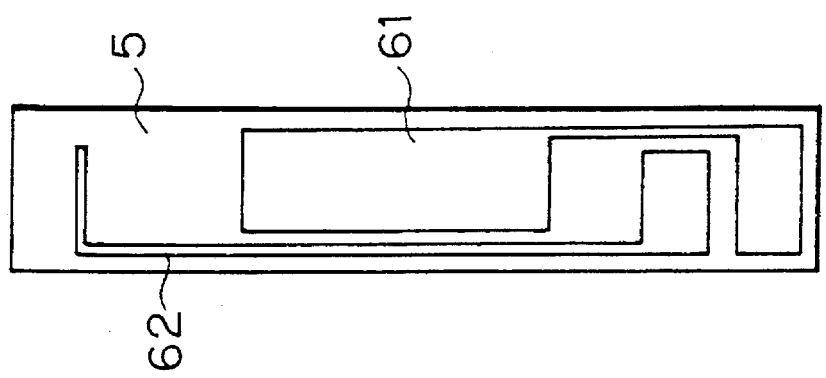

The electrode was fabricated in the following steps:

1. To form the electrode patterns 61 and 62, 400 nm-thick silver patterns were vacuum evaporated onto the polyester sheet 5 through a steel mask after surface treatment agents and toner on the used polyester overhead projection transparency sheet were removed with acetone (FIG. 2A). The chromium or titanium adhesive layer often used in forming noble metal patterns was not needed to fix the metal electrode patterns to the polyester substrate because the physical adhesion of electrodes pattern metal to the polymer matrix alone was sufficient.

2. The paraffin film 7 was cut and aligned with the electrode pattern and placed and heated on the polyester sheet 5 at 130° C. (FIG. 2B).

3. The recycled copier paper 8 was cut to fit the electrolyte pattern and placed on the surface of the polyester sheet 5 in an area free of the paraffin film pattern.

Figure 4:
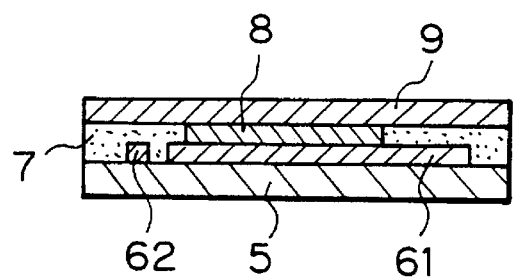

2. The FEP membrane was patterned to form a gas permeable membrane 9. To strengthen membrane adhesion, the surface of the membrane 9 was processed before the patterning. The patterns of the membrane 9, paraffin 7, and paper 8 were aligned and the polyester sheet 5 was then pressed to eliminate gaps between the paper 8 and other layers at 130° C. (FIGS. 3 and 4).

5. Each oxygen electrode was cut using scissors or a razor blade.

6. The paper was saturated with an electrolyte by immersing the chip in an electrolyte solution. To eliminate bubbles between the FEP membrane or polyester sheet and paper due to uneven permeation, the chip and electrolyte solution were put in a container in a chamber which air was evacuated.

Because no special cutter were used for the paper, paraffin film, and FEP membrane, the electrodes in the experiments were made individually and chips were diced following step 1. Such cutters would, of course, enable batch-fabrication to the final stage. The 21 cm×15 cm sheet used yielded 190 chips, but larger sheets can be used so long as the vacuum chamber can hold them. The sheets can be used so long as the vacuum chamber can hold them. The micromachining used in previous work requires about two weeks for an oxygen electrode to be completed. This time, however, the process required only one person one day to complete all processes.

Procedure

In all experiments, a well-stirred 10 mM phosphate buffer solution (pH 7.0) at 25° C., with oxygen saturated in air, was used. A constant voltage was applied and the current detected using a potentiostat (HA-501G, Hokuto Denko). To prevent operation stability from being adversely affected by hydrogen peroxide intermediate remaining following oxygen reduction, a relatively high voltage of −0.9 V was applied against the Ag/AgCl anode. To evaluate the oxygen electrode's response, the dissolved oxygen concentration was changed stepwise by adding $Na_2SO_3$. The oxygen electrode was calibrated using a dissolved-oxygen meter (TOA Electronics DO-1B). Before measurement, the oxygen electrode's sensitive area was immersed in an oxygen-free $Na_2SO_3$ solution and −0.9 V were applied for about 10 minutes to activate the cathode surface.

Results

Response profile

Figure 5:
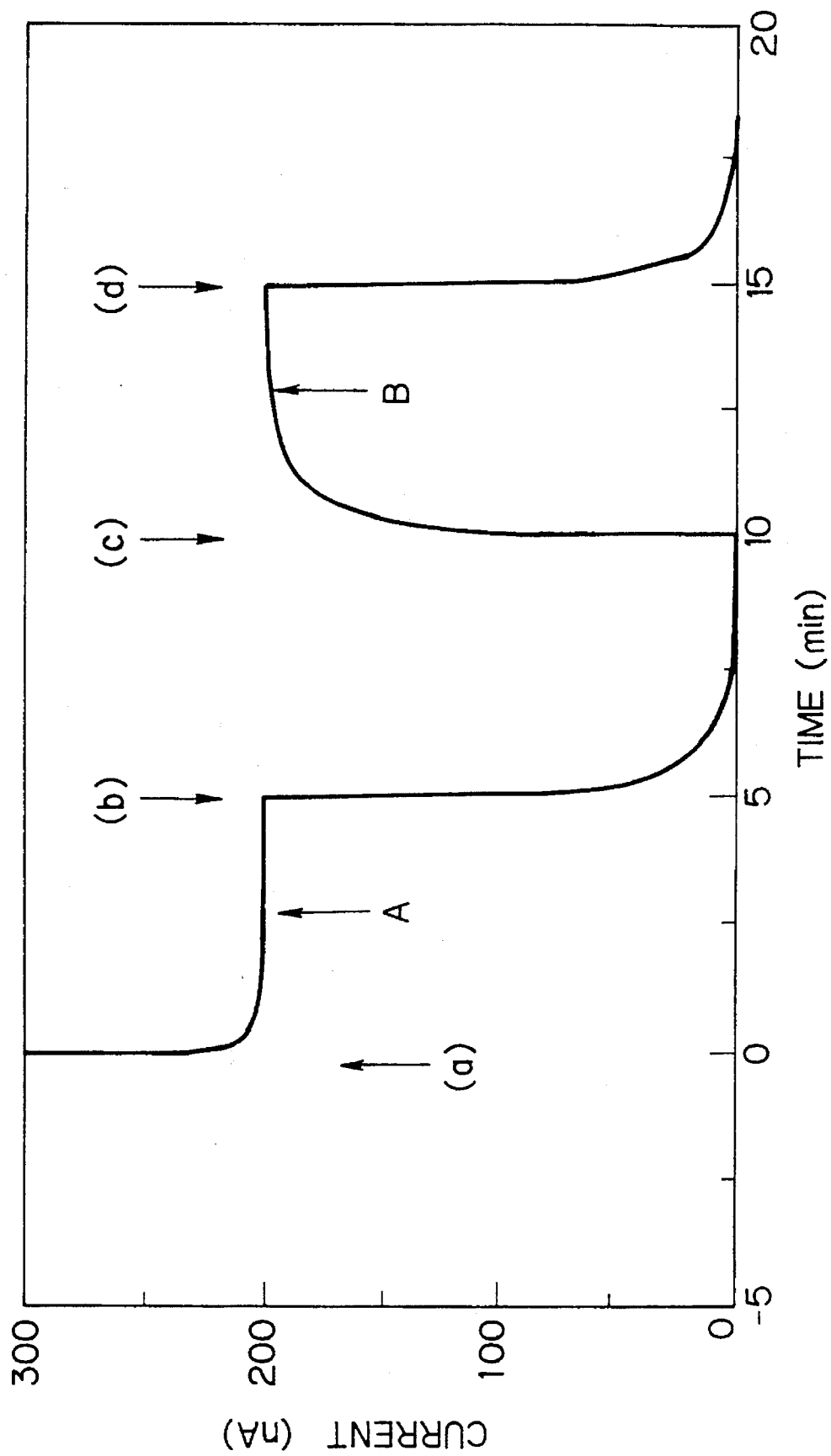
FIG. 5 shows the response speed of an oxygen electrode in an Example of the present invention.

A single-use disposable sensor must reach the equilibrium as soon as possible after a voltage is applied. The current was stabilized 1 min after the voltage was impressed. $Na_2SO_3$ was added after 5 min to remove dissolved oxygen. The oxygen electrode was stabilized in the oxygen-free buffer solution in 5 minutes, then its sensitive area was moved into an oxygen-saturated buffer solution, and $Na_2SO_3$ was added again to remove dissolved oxygen. Despite its simplicity, the oxygen electrode gives a very clear response curve (FIG. 5). When the oxygen concentration was changed from saturation level (A) to zero (b), a 90% response time was between 60 to 70 seconds. For a reverse change from oxygen zero (c) to saturation (B), the response time was also distributed between 60 and 70 seconds. The response time is mainly determined by oxygen diffusion through the paper, and was voltage dependent, becoming shorter when the voltage increased to −0.9 V; at −0.6 V, for example, the response was several times slower. This is probably due to difference of the reduction rate of hydrogen peroxide intermediate.

Some differences are often observed in current levels at oxygen saturation (A and B in FIG. 5). They are probably due to either remaining air bubbles or hydrogen peroxide produced after the voltage is impressed. Operating the oxygen electrode in an oxygen-free $Na_2SO_3$ solution for more than 10 min caused levels to coincide and speeded up the response.

The negligible residual current at an oxygen concentration of zero clearly indicated that an electrochemical crosstalk between the cathode and anode had a short-term effect. A larger residual current, observed when the voltage was relatively low, was removed by operating the oxygen electrode in a $Na_2SO_3$ solution for several hours, which suggests the advantage of operating the oxygen electrode at a relatively high voltage.

Calibration curve

Figure 6:
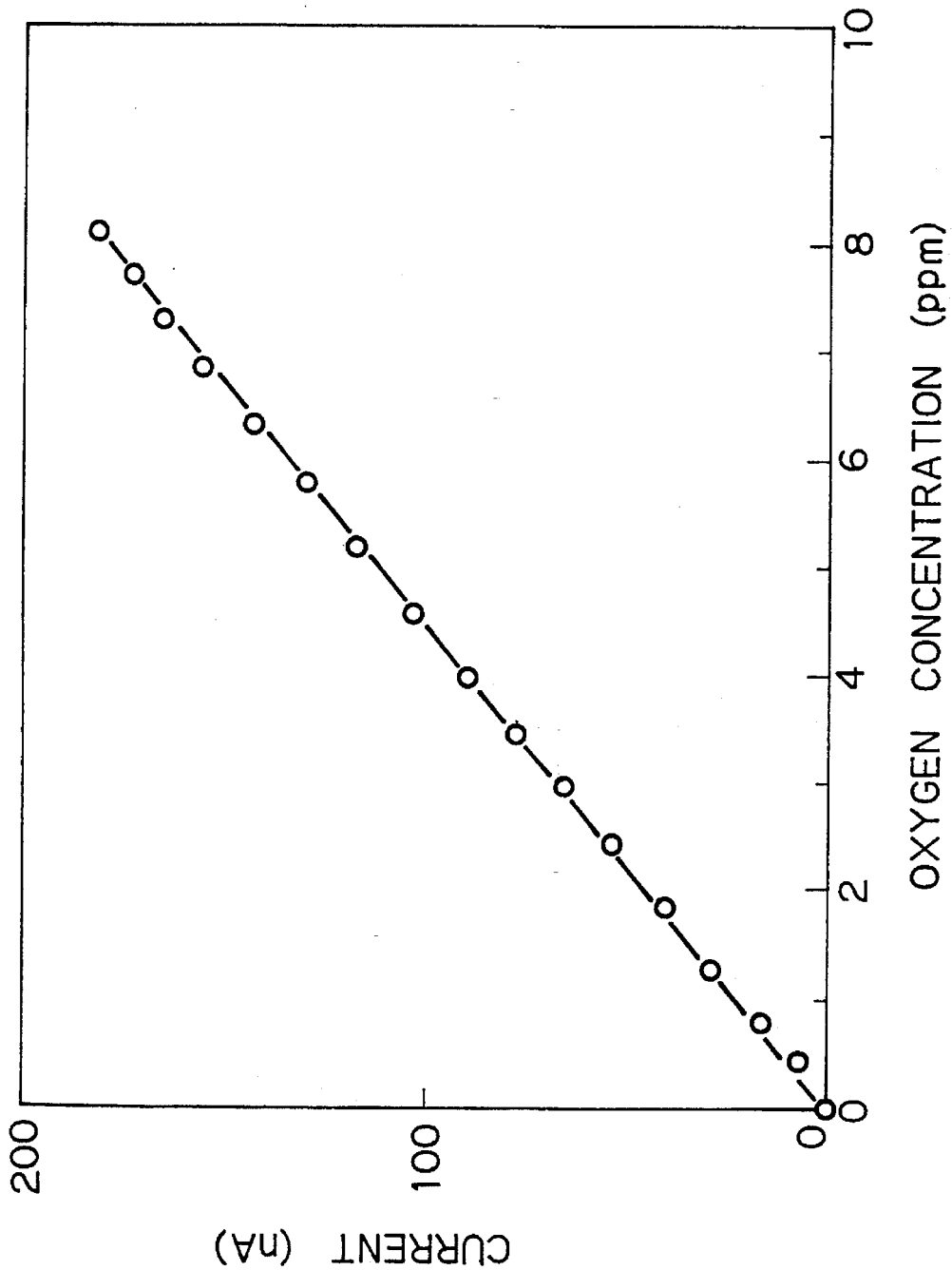
FIG. 6 is a graph showing the detectable electric current vs. the oxygen concentration for an oxygen electrode in an Example of the present invention.

The oxygen electrode showed a very good linear relationship between the generated current and dissolved oxygen concentration, indicating that the crosstalk between the cathode and anode is negligible and that the oxygen electrode is usable as a biosensor transducer (FIG. 6). The current at the oxygen saturation was between 180 nA and 210 nA. This small variation of performance among oxygen electrodes, along with the excellent proportional relationship starting from the origin, ensures easy calibration.

Stability

The fairly rapid evaporation of the electrolyte solution through the gas permeable membrane may result in the absorption of water inside the paper and the formation of an air layer between the paper and the gas permeable membrane. If air reaches the cathode, the electrodes tend to break within two hours due to a sudden current increase. This problem may be solved by covering the anode area and the entrance area of the electrolyte with a paraffin film.

Figure 7:
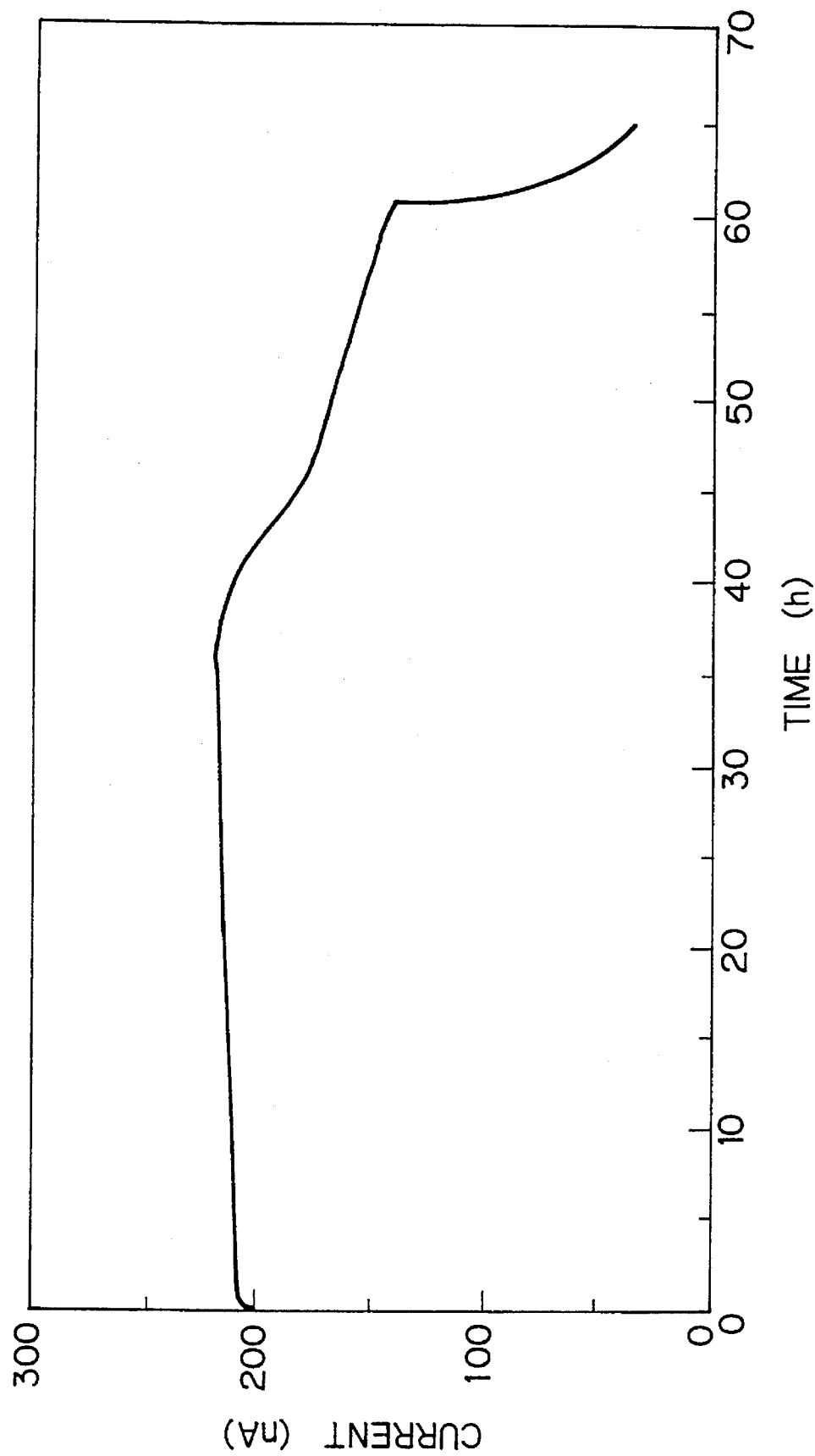
FIG. 7 shows the output current stability at oxygen saturation.

Regarding output current stability at oxygen saturation (FIG. 7), when the voltage was −0.9 V, the output current was very stable and the oxygen electrode worked for 62 hours, followed by a sudden current decrease when the electrode was broken. Prior to 40 hours of operation, the current fluctuation was less than 1%/h and was surprisingly stable with this kind of miniature electrode. By observing the broken electrode from transparent backside, it was seen that almost all of the anode was consumed. In the oxygen electrodes, the two tendencies were observed when the electrode were broken: a sudden current increase and decrease. The increase was caused by an electrochemical crosstalk between the detecting electrodes. The decrease was caused by a chlorine ion depletion or silver consumption in the anode. The current decrease in FIG. 7 suggests that electrochemical crosstalk can be neglected here.

Thus, the present invention provides a remarkably inexpensive disposable Clark oxygen electrode fabricable with cheap materials, particularly recycled materials, and without expensive photographic or micromachining processes. The sensor consists of recycled polyester overhead projection transparencies on which the cathode and anode patterns are deposited by vacuum evaporation, recycled copier paper to hold the electrolyte, and a gas-permeable membrane.

Although deceptive simple in terms of structure and fabrication, the electrode performed well as an oxygen sensor and proved surprisingly durable: its 90% response time was between 60 and 70 seconds, with a good linear relationship between generated current and dissolved oxygen concentration. Although designed to be disposed of after one use, the electrode decomposed a lifespan exceeding 60 hours, with very low current drift.

B. Oxygen electrode (2)

The above small oxygen electrode exhibited a good response as an oxygen electrode, but it was also found that gas bubbles (oxygen) tended to be trapped in a space between the electrolyte layer, i.e., the paper 8 impregnated with the electrolyte, and the gas permeable membrane 9, and this trapped gas moved to the cathode, thereby making the out put electric current very unstable. As a result, most oxygen electrodes as manufactured as above were damaged with a rapid increase of the out put electric current within about 30 minutes after the application of voltage. Further, an electric current increase in the form of a spike is sometimes seen even during stable operation period. Thus, the life time of the above oxygen electrode should be preferably improved.

This problem can be solved by impregnating the electrolyte layer or the paper 8 with a gel. The gel is swollen when an electrolyte is introduced into the paper 8 so that a space between the electrolyte layer or the paper 8 and the gas permeable membrane 9 is filled with the swollen gel.

More specifically, an oxygen electrode as described above was manufactured but, before the paper 8 was assembled with the polyester sheet 5, the paper 8 was immersed in 0.4%—sodium alginate and then dried. The paper was then immersed in 0.1M—potassium chloride solution, allowed to be placed for a while and dried. The thus obtained paper was placed on the polyester sheet 5 in a central region surrounded by the paraffin layer 7, as shown in FIG. 2C. Then the gas permeable membrane 9 was disposed over them.

The thus obtained oxygen electrode was immersed in an aqueous electrolyte solution and, as a result, the electrolyte was impregnated up to the tip or the sensitive portion of the electrode in about 10 minutes. When bubbles remained in the sensitive portion, the small oxygen electrode immersed in an aqueous electrolyte solution, as a whole, was placed in a vacuum chamber and a vacuum was applied to effect a degassing. The used electrolyte was, for example, 0.1M-potassium chloride in 50 mM Tris/HCl buffer solution (pH 8.5).

For example, the sensitive portion of the finished oxygen electrode was immersed in a buffer solution and, while a constant voltage (e.g., −0.9 V to the working electrode) was being applied between the cathode 62 and anode 61, the electric current generated from the cathode 62 by the reduction of the oxygen was measured.

By impregnation with a gel, the response of the oxygen electrode was made stable and the life time was extended to 2 to 3 hours, in comparison with the short life time of about 30 minutes when the paper was not impregnated with a gel.

C. Biosensor

Figure 8:
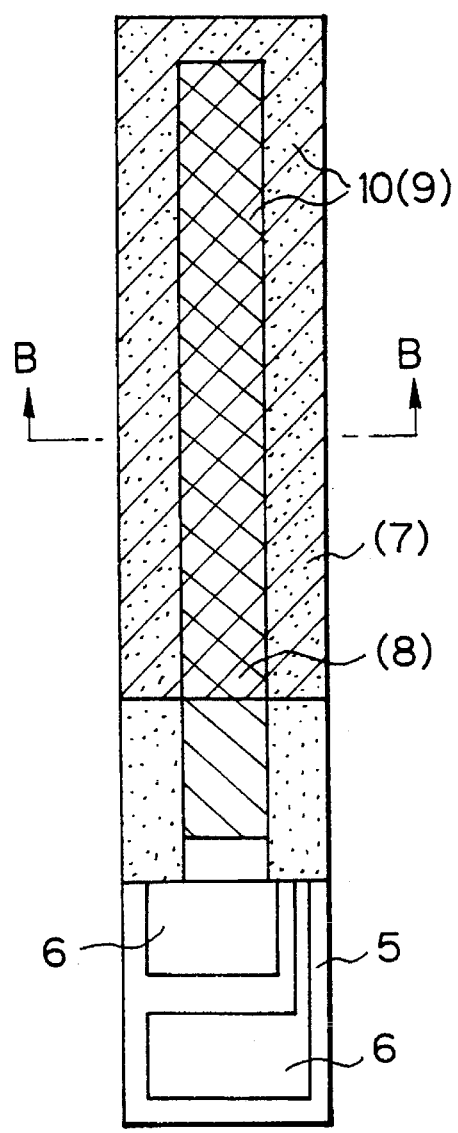
FIGS. 8 and 9 are plan and cross-sectional views of a biosensor in an Example of the present invention.
Figure 9:
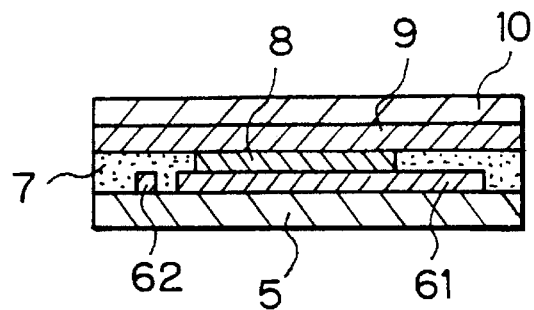

Referring to FIGS. 8 and 9, a biosensor may be obtained by mixing and coating a solution of 5 mg of an autotrophic microorganism using carbon dioxide gas as a nutrient or an enzyme such as glucose oxidase with 20 µl of 10%—bovine serum albumin solution and 20 µl of 10%—glutaraldehyde on the gas permeable membrane 9 of the above oxygen electrode, to immobilize the same or form an enzyme or microorganism-immobilized layer 10. FIG. 8 is a plan view and FIG. 9 is a cross sectional view of the biosensor cut along the line B—B in FIG. 8.

In this biosensor, for example, if an autotrophic microorganism taking carbon dioxide gas as a nutrient is immobilized, the oxygen amount consumed in linear relationship with the consumption of carbon dioxide gas may be measured to determine the concentration of the carbon dioxide gas and, if glucose oxidase is immobilized, the oxygen amount consumed in linear relationship with the oxidation of glucose oxidase may be measured to determine the concentration of the sugar.

This biosensor is also very cheap and can be used as a disposable product.

What we claim are:

1. An oxygen electrode comprising:

a plastic sheet having a planar surface;

an Ag/AgCl anode pattern on said surface of the plastic sheet;

a first electrode lead and pad pattern formed on the surface of the plastic sheet and electrically connected to said anode pattern;

a cathode pattern formed on said surface of the plastic sheet;

a second electrode lead and pad pattern formed on the surface of the plastic sheet and electrically connected to said cathode pattern;

a paraffin layer located on said surface of the plastic sheet over said patterns, said paraffin layer comprising a paraffin having a softening point of about 100° to 150° C. and being configured so as to delineate a sensitive area of the plastic sheet where portions of said anode and cathode patterns are exposed;

a carrier sheet formed of a natural or synthetic paper or a woven or non-woven cloth overlying said sensitive area and contacting said portions of the anode and cathode patterns; and a gas permeable membrane overlying a first portion of the carrier sheet and the paraffin layer, said membrane being positioned and configured so that there is a second portion of the carrier sheet which is not covered by the membrane, whereby an electrolyte solution may be impregnated through said second portion of the carrier sheet.

2. An oxygen electrode according to claim 1, wherein the plastic sheet is formed from polyester, polycarbonate, polyimide or polystyrene.

3. An oxygen electrode according to claim 1, wherein the gas permeable membrane is formed from a fluorinated ethylene propylene, a silicone rubber, polypropylene or polytetrafluoroethylene.

4. An oxygen electrode comprising:

a plastic sheet having a planar surface;

an Ag/AgCl anode pattern on said surface of the plastic sheet;

a first electrode lead and pad pattern formed on the surface of the plastic sheet and electrically connected to said anode pattern;

a cathode pattern formed on said surface of the plastic sheet;

a second electrode lead and pad pattern formed on the surface of the plastic sheet and electrically connected to said cathode pattern;

a paraffin layer located on said surface of the plastic sheet over said patterns, said paraffin layer comprising a paraffin having a softening point of about 100° to 150° C. and being configured so as to delineate a sensitive area of the plastic sheet where portions of said anode and cathode patterns are exposed;

a carrier sheet formed of a natural or synthetic paper or a woven or non-woven cloth overlying said sensitive area and contacting said portions of the anode and cathode patterns, said carrier sheet being impregnated with a gel; and a gas permeable membrane overlying a first portion of the carrier sheet and the paraffin layer, said membrane being positioned and configured so that there is a second portion of the carrier sheet which is not covered by said membrane, whereby an electrolyte solution may be impregnated through said second portion of the carrier sheet.

5. An oxygen electrode as set forth in claim 4, wherein said gel comprises agarose, gelatin, polyacrylamide or calcium alginate.

6. An biosensor comprising:

a plastic sheet having a planar surface;

an Ag/AqCl anode pattern on said surface of the plastic sheet;

a first electrode lead and pad pattern formed on the surface of the plastic sheet and electrically connected to said anode pattern;

a cathode pattern formed on said surface of the plastic sheet;

a second electrode lead and pad pattern formed on the surface of the plastic sheet and electrically connected to said cathode pattern;

a paraffin layer located on said surface of the plastic sheet over said patterns, said paraffin layer comprising a paraffin having a softening point of about 100° to 150° C. and being configured so as to delineate a sensitive area of the plastic sheet where portions of said anode and cathode patterns are exposed;

a carrier sheet formed of a natural or synthetic paper or a woven or non-woven cloth overlying said sensitive area and contacting said portions of the anode and cathode patterns;

a gas permeable membrane overlying a first portion of the carrier sheet and the paraffin layer, said membrane being positioned and configured so that there is a second portion of the carrier sheet which is not covered by said membrane, whereby an electrolyte solution can be impregnated through said second portion of the carrier sheet; and an enzyme or microorganism-immobilized layer on the gas permeable membrane.

7. A process for manufacturing an oxygen electrode comprising:

preparing a plastic sheet having a planar surface;

forming an Ag/AqCl anode pattern on said surface of the plastic sheet;

forming a first electrode lead and pad pattern that is electrically connected to said anode pattern on the surface of the plastic sheet;

forming a cathode pattern on said surface of the plastic sheet;

forming a second electrode lead and pad pattern that is electrically connected to said cathode pattern on the surface of the plastic sheet and;

fusing a paraffin layer onto said surface of the plastic sheet over said patterns, said paraffin layer comprising a paraffin having a softening point of about 100° to 150° C.;

configuring said paraffin layer so as to delineate a sensitive area of the plastic sheet where portions of the anode and cathode patterns are exposed;

placing a carrier sheet formed of a natural or synthetic paper or a woven or non-woven cloth on the plastic sheet so as to overlie said sensitive area and contact said portions of the anode and cathode patterns;

placing a gas permeable membrane over a first portion of the carrier sheet and the paraffin layer, said membrane being positioned and configured so that there is a second portion of the carrier sheet which is not covered by said membrane; and impregnating the carrier sheet with an electrolyte through said second portion of the carrier sheet.

8. A process according to claim 7, including forming the anode pattern by selective vacuum evaporation of a metal with a metal mask.

9. A process according to claim 7, including forming the cathode pattern by selective vacuum evaporation of a metal with a metal mask.

10. A process according to claim 7, including forming the anode and cathode patterns by selective vacuum evaporation of a metal with a metal mask.

11. A process for manufacturing an oxygen electrode comprising:

preparing a plastic sheet having a planar surface;

forming an Ag/AgCl anode pattern on said surface of the plastic sheet;

forming a first electrode lead and pad pattern that is electrically connected to said anode pattern on the surface of the plastic sheet;

forming a cathode pattern on said surface of the plastic sheet;

forming a second electrode lead and pad pattern that is electrically connected to said cathode pattern on the surface of the plastic sheet and;

fusing a paraffin layer onto said surface of the plastic sheet over said patterns, said paraffin layer comprising a paraffin having a softening point of about 100° to 150° C.;

configuring said paraffin layer so as to delineate a sensitive area of the plastic sheet where portions of the anode and cathode patterns are exposed;

placing a carrier sheet formed of a natural or synthetic paper or a woven or non-woven cloth on the plastic sheet so as to overlie said sensitive area and contact said portions of the anode and cathode patterns;

impregnating the carrier sheet with a gel;

placing a gas permeable membrane over a first portion of the carrier sheet and the paraffin layer, said membrane being positioned and configured so that there is a second portion of the carrier sheet which is not covered by said membrane; and impregnating the carrier sheet with an electrolyte through said second portion of the carrier sheet.

12. A process as set forth in claim 11, wherein said gel comprises agarose, gelatin, polyacrylamide or calcium alginate.

13. A process for manufacturing a biosensor comprising:

preparing a plastic sheet having a planar surface;

forming an Ag/AgCl anode pattern on said surface of the plastic sheet;

forming a first electrode lead and pad pattern that is electrically connected to said anode pattern on the surface of the plastic sheet;

forming a cathode pattern on said surface of the plastic sheet;

forming a second electrode lead and pad pattern that is electrically connected to said cathode pattern on the surface of the plastic sheet and;

fusing a paraffin layer onto said surface of the plastic sheet over said patterns, said paraffin layer comprising a paraffin having a softening point of about 100° to 150° C.;

configuring said paraffin layer so as to delineate a sensitive area of the plastic sheet where portions of the anode and cathode patterns are exposed;

placing a carrier sheet formed of a natural or synthetic paper or a woven or non-woven cloth on the plastic sheet so as to overlie said sensitive area and contact said portions of the anode and cathode patterns;

placing a gas permeable membrane over a first portion of the carrier sheet and the paraffin layer, said membrane being positioned and configured so that there is a second portion of the carrier sheet which is not covered by said membrane;

forming an enzyme or microorganism-immobilized layer on the gas permeable membrane; and impregnating the carrier sheet with an electrolyte through said second portion of the carrier sheet.

14. A biosensor comprising:

a plastic sheet having a planar surface;

an Ag/AgCl anode pattern on said surface of the plastic sheet;

a first electrode lead and pad pattern formed on the surface of the plastic sheet and electrically connected to said anode pattern;

a cathode pattern formed on said surface of the plastic sheet;

a second electrode lead and pad pattern formed on the surface of the plastic sheet and electrically connected to said cathode pattern;

a paraffin layer located on said surface of the plastic sheet over said patterns, said paraffin layer comprising a paraffin having a softening point of about 100° to 150° C. and being configured so as to delineate a sensitive area of the plastic sheet where portions of said anode and cathode patterns are exposed;

a carrier sheet formed of a natural or synthetic paper or a woven or non-woven cloth overlying said sensitive area and contacting said portions of the anode and cathode patterns, said carrier sheet being impregnated with a gel;

a gas permeable membrane overlying a first portion of the carrier sheet and the paraffin layer, said membrane being positioned and configured so that there is a second portion of the carrier sheet which is not covered by said membrane, whereby an electrolyte solution can be impregnated through said second portion of the carrier sheet; and an enzyme or microorganism-immobilized layer on the gas permeable membrane.

15. An oxygen electrode as set forth in claim 14, wherein said gel comprises agarose, gelatin, polyacrylamide or calcium alginate.

16. A process for manufacturing a biosensor comprising:

preparing a plastic sheet having a planar surface;

forming an Ag/AgCl anode pattern on said surface of the plastic sheet;

forming a first electrode lead and pad pattern that is electrically connected to said anode pattern on the surface of the plastic sheet;

forming a cathode pattern on said surface of the plastic sheet;

forming a second electrode lead and pad pattern that is electrically connected to said cathode pattern on the surface of the plastic sheet and;

fusing a paraffin layer onto said surface of the plastic sheet over said patterns, said paraffin layer comprising a paraffin having a softening point of about 100° to 150° C.;

configuring said paraffin layer so as to delineate a sensitive area of the plastic sheet where portions of the anode and cathode patterns are exposed;

placing a carrier sheet formed of a natural or synthetic paper or a woven or non-woven cloth on the plastic sheet so as to overlie said sensitive area and contact said portions of the anode and cathode patterns;

impregnating the carrier sheet with a gel;

placing a gas permeable membrane over a first portion of the carrier sheet and the paraffin layer, said membrane being positioned and configured so that there is a second portion of the carrier sheet which is not covered by said membrane;

forming an enzyme or microorganism-immobilized layer on the gas permeable membrane; and impregnating the carrier sheet with an electrolyte through said second portion of the carrier sheet.

17. A process as set forth in claim 16, wherein said gel comprises agarose, gelatin, polyacrylamide or calcium alginate.

* * * * *